(12) United States Patent
Duda

(10) Patent No.: US 9,387,125 B1
(45) Date of Patent: Jul. 12, 2016

(54) SOCK FOR TREATMENT OF FOOT AND LEG WOUNDS, METHODS OF USE AND MANUFACTURE

(71) Applicant: Vive Wear LLC, Greensboro, NC (US)

(72) Inventor: Marcus Duda, Greensboro, NC (US)

(73) Assignee: VIVE WEAR LLC, Greensboro, NC (US)

( * ) Notice: Subject to any disclaimer, the term of this patent is extended or adjusted under 35 U.S.C. 154(b) by 0 days.

(21) Appl. No.: 15/006,781

(22) Filed: Jan. 26, 2016

(51) Int. Cl.
- *A61F 13/00* (2006.01)
- *A61F 13/08* (2006.01)
- *A61F 13/06* (2006.01)
- *A61N 1/32* (2006.01)

(52) U.S. Cl.
CPC ..... *A61F 13/00063* (2013.01); *A61F 13/00017* (2013.01); *A61F 13/064* (2013.01); *A61F 13/066* (2013.01); *A61F 13/069* (2013.01); *A61F 13/08* (2013.01); *A61N 1/326* (2013.01); *A61F 2013/00093* (2013.01); *A61F 2013/00119* (2013.01); *A61F 2013/00285* (2013.01)

(58) Field of Classification Search
CPC ............. A61N 1/326; A61F 2013/00093; A61F 2013/00119; A61F 2013/00285; A61F 2013/00012
USPC .......................................................... 28/167
See application file for complete search history.

(56) References Cited

U.S. PATENT DOCUMENTS

| | | |
|---|---|---|
| 4,206,514 A | 6/1980 | Yamauchi |
| 4,378,226 A | 3/1983 | Tomibe et al. |
| 4,852,453 A * | 8/1989 | Morin .................. D01F 11/127 |
| | | 102/505 |
| 5,458,906 A | 10/1995 | Liang |
| 5,496,860 A | 3/1996 | Matsumoto et al. |
| 5,898,948 A * | 5/1999 | Kelly ..................... A41B 11/00 |
| | | 2/239 |
| 6,124,221 A | 9/2000 | Gabbay |
| 6,522,918 B1 * | 2/2003 | Crisp ...................... A61N 1/30 |
| | | 604/20 |
| 6,946,196 B2 | 9/2005 | Foss |
| 6,979,491 B2 | 12/2005 | Yan et al. |

(Continued)

FOREIGN PATENT DOCUMENTS

| | | |
|---|---|---|
| WO | WO 2008/007908 | 1/2008 |
| WO | WO 2013/106410 | 7/2013 |
| WO | WO 2014/057285 | 4/2014 |

OTHER PUBLICATIONS

"Men's Recovery Compression Calf Sleeve," [online], Dec. 15, 2015, <http://www.tommiecopper.com/men-s-recovery-compression-calf-sleeve-2>.

(Continued)

*Primary Examiner* — Kim M Lewis
(74) *Attorney, Agent, or Firm* — Cooley LLP

(57) ABSTRACT

A tubular body is configured to be disposed around and to apply compression to an extremity. The tubular body includes a treatment area having a first filament and a second filament. Both the first filament and the second filament are disposed to engage the surface of the extremity. The first filament includes AgNP in a concentration effective to promote healing of a wound on the surface of the extremity. The second filament includes a metal having a composition that forms a galvanic couple with silver. The first filament and the second filament are arranged in the tubular body such that the AgNP and metal form galvanic couples across at least a portion of the treatment area when in the presence of a fluid in the wound of the extremity that produce an electric current in an amount effective to further promote healing of the wound.

32 Claims, 8 Drawing Sheets

(56) References Cited

U.S. PATENT DOCUMENTS

| | | | | |
|---|---|---|---|---|
| 7,007,517 | B2* | 3/2006 | Menzies | A41B 11/02 66/185 |
| 7,213,420 | B2 | 5/2007 | Lynch et al. | |
| 7,441,419 | B1 | 10/2008 | Dollyhite et al. | |
| 7,457,667 | B2 | 11/2008 | Skiba | |
| 7,552,603 | B2 | 6/2009 | Dahlgren | |
| 7,662,176 | B2* | 2/2010 | Skiba | A43B 1/0045 607/1 |
| 7,950,071 | B2 | 5/2011 | Jeong | |
| 8,075,507 | B2 | 12/2011 | Linnane et al. | |
| 8,224,439 | B2 | 7/2012 | Skiba et al. | |
| 9,220,636 | B2 | 12/2015 | Duda | |
| 2003/0176827 | A1 | 9/2003 | Chandra et al. | |
| 2003/0190851 | A1 | 10/2003 | Yan et al. | |
| 2004/0267237 | A1* | 12/2004 | Sun | A61N 1/044 604/501 |
| 2006/0010574 | A1 | 1/2006 | Linnane et al. | |
| 2006/0253078 | A1* | 11/2006 | Wu | A61M 37/0015 604/173 |
| 2007/0207335 | A1 | 9/2007 | Karandikar et al. | |
| 2007/0283483 | A1 | 12/2007 | Jacober | |
| 2007/0293800 | A1* | 12/2007 | McMaken | A61L 15/44 602/48 |
| 2008/0071204 | A1 | 3/2008 | Linnane et al. | |
| 2008/0249454 | A1 | 10/2008 | Mills | |
| 2009/0025359 | A1 | 1/2009 | Chandra et al. | |
| 2009/0035342 | A1* | 2/2009 | Karandikar | A01N 25/34 424/411 |
| 2009/0280151 | A1 | 11/2009 | Restani et al. | |
| 2010/0069813 | A1* | 3/2010 | Crisp | A61F 13/00008 602/46 |
| 2011/0236343 | A1* | 9/2011 | Chisholm | A01N 59/16 424/78.17 |
| 2013/0178779 | A1* | 7/2013 | Duda | D06M 16/00 602/48 |
| 2014/0276275 | A1* | 9/2014 | Stokes | A61H 1/008 601/84 |
| 2015/0157524 | A1* | 6/2015 | Reid, Jr. | A61H 1/008 601/84 |

OTHER PUBLICATIONS

Abbade, L. P. F. et al., "Venous ulcer: epidemiology, physiopathology, diagnosis and treatment," Int. J. Dermatology, 44(6):449-456 (Jun. 2005).
Atiyeh, B. S. et al., "Effect of silver on burn wound infection control and healing: Review of the literature," Burns, 33(2):139-147 (2007).
Benn, T. M. et al., "Nanoparticle silver released into water from commercially available sock fabrics," Environ. Sci. Technol, 42(11):4133-4139 (Jun. 2008).
Braun, L. et al., "What's new in the literature: An update of new research since the original WHS diabetic foot ulcer guidelines in 2006," Wound Repair and Regeneration 22(5):594-604 (2014).
Cupron, Inc., "About Cupron," Cupron Enhanced, 2008, 6 pages.
Finley, P. J. et al., "Silver dressings improve diabetic wound healing without reducing bioburden," Wounds, 25(10):293-301 (2013).
Gabriel, A. et al. "Reducing bacterial bioburden in infected wounds with vacuum assisted closure and a new silver dressing—a pilot study." Wounds—A Compendium of Clinical Research and Practice 18(9) (2006): 245-255.
Gardner, S. E. et al. "Effect of electrical stimulation on chronic wound healing: a meta-analysis." Wound Repair and Regeneration, 7(6):495-503 (1999).
Garduque, Gian et al. "Silver as an Antimicrobial Agent—MicrobeWiki." Silver as an Antimicrobial Agent. MicrobeWiki, 2010. Web. Retrieved Feb. 24, 2016. <http://microbewiki.kenyon.edu/index.php/Silver_as_an_Antimicrobial_Agent.
Hatchett, D. W. et al., "Electrochemistry of sulfur adlayers on the low-index faces of silver," The Journal of Physical Chemistry, 100(23):9854-9859 (1996).
Herber, O. R. et al., "A systematic review on the impact of leg ulceration on patients' quality of life," Health and Quality of Life Outcomes, 5:44 (Jul. 2007), Published online Jul. 25, 2007.

Impellitteri, C. A. et al., "The speciation of silver nanoparticles in antimicrobial fabric before and after exposure to a hypochlorite/detergent solution," Journal of Environmental Quality, 38:1528-1530 (2009).
International Search Report and Written Opinion for International Application No. PCT/US2013/020803, mailed Jun. 27, 2013, 7 pages.
Johannes, L., "Silver lining to fighting germs," The Wall Street Journal [online], Jul. 19, 2011, 3 pages.
Jorgensen, J. H. et al. "Antimicrobial susceptibility testing: a review of general principles and contemporary practices." Clinical infectious diseases 49: 1749-1755 (2009).
Jünger, M. et al. "Local therapy and treatment costs of chronic, venous leg ulcers with electrical stimulation (Dermapulse®): a prospective, placebo controlled, double blind trial." Wound repair and regeneration 16: 480-487 (2008).
Kawasaki, L. et al. "The mechanisms and evidence of efficacy of electrical stimulation for healing of pressure ulcer: a systematic review," Wound Repair and Regeneration, 22(2):161-173 (2014).
Kelly, F. M. et al., "Functionalised hybrid materials of conducting polymers with individual wool fibers," Journal of Nanoscience and Nanotechnology, 8(4):1965-1972 (2008).
Kirsner, R. S. et al., "Matrix metalloproteinases in normal and impaired wound healing: a potential role of nanocrystalline silver," Wounds, 13:4-12 (2002).
Kloth, L. C., "Electrical stimulation technologies for wound healing," Adv. Wound Care (New Rochelle), 3(2):81-90 (2014).
Koel, G. et al.. "Electrostimulation: current status, strength of evidence guidelines, and meta-analysis." Advances in wound care 3.2 (2014): 118-126.
Ladwig, G. P. et al., "Ratios of activated matrix metalloproteinase-9 to tissue inhibitor of matrix metalloproteinase-1 in would fluids are inversely correlated with healing of pressure ulcers," Wound Repair and Regeneration, 10(1):26-37 (Jan. 2002).
Liu, X. et al., "Resistance to compression behavior of alpaca and wool," Textile Research Journal, 74(3):265-270 (2004).
Liu, Y. et al., "Increased matrix metalloproteinase-9 predicts poor wound healing in diabetic foot ulcers," Diabetes Care, 32(1):117-119 (Jan. 2009).
Longo, A. et al., "Dependence of optical and microstructure properties of thiol-capped silver nanoparticles embedded in polymeric matrix," Polymers, 3(4):1794-1804 (2011).
McCarty, S. M. et al., "The role of endogenous and exogenous enzymes in chronic wounds: A focus on the implications of aberrant levels of both host and bacterial proteases in wound healing," Wound Repair and Regeneration, 20(2):125-136 (2012).
Nair, L. S. et al., "Silver nanoparticles: Synthesis and therapeutic applications," Journal of Biomedical Nanotechnology, 3(4):301-316 (2007).
Office Action for U.S. Appl. No. 13/737,424, mailed Feb. 20, 2015, 9 pages.
Pal, S. et al., "Does the antibacterial activity of silver nanoparticles depend on the shape of the nanoparticle? A study of the gram-negative bacterium *Escgerichia coli*," Applied and Environmental Microbiology, 73(6):1712-1720 (Mar. 2007).
Palfreyman, S. J. et al., "Dressings for healing venous leg ulcers," Chochrane Database Syst. Rev., (3):CD001103 (Jul. 2006).
Percival, S. L. et al., "Antimicrobial activity of silver-containing dressings on wound microorganisms using an in vitro biofilm model,", Int. Wound J., 4(2):186-191 (2007).
Percival, S. L. et al., "Assessing the effect of an antimicrobial wound dressing on biofilms." Wound Repair and Regeneration, 16(1):52-57 (2008).
Pfurtscheller, K. et al., "Transdermal uptake and organ distribution of silver from two different wound dressings in rats after a burn trauma," Wound Repair and Regeneration, 22(5):654-659 (2014).
Prakash, S. et al. "Venous Ulcer: Review Article" Surgical Science, 2013, 4, 144-150.
Rayment, E. A. et al., "Increased matrix metalloproteinase-9 (MMP-9) activity observe in chronic wound fluid is related to the clinical severity of the ulcer," Br. J. Dermatol., 158(5):951-961 (May 2008).

(56) References Cited

OTHER PUBLICATIONS

Reiss, M. J. et al., "α1-Antichymotrypsin activity correlates with and may modulate matrix metalloproteinase-9 in human acute wounds," Wound Repair and Regeneration, 17(3):418-426 (May/Jun. 2009).

Sun, R. W. et al., "Silver nanoparticles fabricated in Hepes buffer exhibit cytoprotective activities toward HIV-1 infected cells," Chem. Commun. (Camb.), 40:5059-5061 (2005).

Tang, B. et al., "Application of anisotropic silver nanoparticles: Multifunctionalization of wool fabric," Journal of Colloid and Interface Science, 356(2):513-518 (2011).

Thawer, H. et al. "Effects of electrical stimulation on the histological properties of wounds in diabetic mice." Wound Repair and Regeneration 9.2 (2001): 107-115.

Tian, J. et al., "Topical delivery of silver nanoparticles promotes wound healing," ChemMedChem., 2(1):129-136 (Jan. 2007).

Trengove, N. J. et al., "Analysis of the acute and chronic would environments: the role of proteases and their inhibitors," Wound Repair and Regeneration, 7(6):442-452 (1999).

Trial, C. et al., "Assessment of the antimicrobial effectiveness of a new silver alginate wound dressing: a RCT," Journal of Wound Care, 19(1):20-26 (Jan. 2010).

Valencia, I. C. et al., "Chronic venous insufficiency and venous leg ulceration," Journal of the American Academy of Dermatology, 44(3):401-421 (Mar. 2001).

Varner, K. et al., "State of the Science Literature Review: Everything Nanosilver and More," Scientific, Technical, Research, Engineering and Modeling Support Final Report, Contract No. EP-C-05-057, Task Order No. 95, U.S. Environmental Protection Agency, (Aug. 2010), 221 pages.

Widgerow, A. D., "Nanocrystalline silver, gelatinases and the clinical implications," Burns, 36(7):965-974 (2010).

Wijnhoven, S. W. P. et al., "Nano-silver—a review of available data and knowledge gaps in human and environmental risk assessment," Nanotoxicology, 3(2):109-138 (Jun. 2009).

Wong, K. K. Y. et al., "Further evidence of the anti-inflammatory effects of silver nanoparticles," ChemMedChem., 4:1129-1135 (2009).

Wright, J. B. et al., "Early healing events in a porcine model of contaminated wounds: effects of nanocrystalline silver on matrix metalloproteinases, cell apoptosis, and healing," Wound Repair Regen., 10(3):141-151 (2002).

Wright, J. B. et al., "Efficacy of topical silver against fungal burn wound pathogens," Am. J. Infect. Control, 27(4):344-350 (Aug. 1999).

Wright, J. B. et al., "Wound management in an era of increasing bacterial antibiotic resistance: A role for topical silver treatment," American Journal of Infection Control, 26(6):572-577 (Dec. 1998).

Yager, D. R. et al., "Wound fluids from human pressure ulcers contain elevated matrix metalloproteinase levels and activity compared to surgical wound fluids," J. Invest. Dermatol., 107(5):743-748 (1996).

Yager, D. R., "Wound fluids: A window into the wound environment?", The International Journal of Lower Extremity Wounds, 6(4):262-272 (Dec. 2007).

* cited by examiner

100

SOCK FOR TREATMENT OF FOOT AND LEG WOUNDS, METHODS OF USE AND MANUFACTURE

BACKGROUND

Leg ulceration is the most prevalent chronic wound in Western countries, affecting about 1 to 2% of the adult population (Valencia I C, Falabella A, Kirsner R S, Eaglstein W H. Chronic venous insufficiency and venous leg ulceration. J Am Acad Dermatol 2001; 44: 401-21). The main causes of leg ulceration are venous hypertension, arterial insufficiency, and diabetes. Venous ulcers account for approximately 80% of all leg ulcers and are the result of venous hypertension. The current treatment for venous ulcers includes graduated compression support stockings or compression bandaging of the limb. Despite the standard of care of compression therapy, 50 to 70% of venous leg ulcers remain unhealed after 12 weeks of treatment and 54 to 78% of ulcers will reoccur (Abbade L P, Lastoria S. Venous ulcer: epidemiology, physiopathology, diagnosis and treatment. Int Wound J 2006; 3:113-20). These chronic wounds have a treatment cost in the United States of approximately one billion dollars per year and have a significant impact on the patient's quality of life (Herber O R, Schnepp W, Rieger M A. A systemic review on the impact of leg ulceration on patient's quality of life. Health Qual Life Outcomes 2007; 5: 44).

The biology of the chronic venous and diabetic wounds is quite different from acute wounds. In an acute wound the initial fibrin clot provides hemostasis and the platelets release cytokines, growth factors, and recruit inflammatory cells. The recruitment of inflammatory cells includes neutrophils and macrophages to eradicate bacteria. At the leading edge of the wound the protease cut through the fibrin clot. Matrix Metalloproteinases (MMP) are up regulated by the keratinocyte to cut a path through the matrix proteins to allow the keratinocyte to advance and close the wound. MMP-9 (gelatinase B) cuts through the basal lamina collagen (type IV) and anchoring collagen (type VII) to allow the keratinocytes to advance and close the wound. Once the keratinocytes cover the wound, the wound is re-epithelized, the basal lamina is reestablished and the MMP-9 is shut off.

However, in a chronic wound, the MMP-9 is not shut off. The elevated levels of this protease continue to destroy the wound matrix that is produced to heal the wound. The level of MMP-9 in a chronic wound can be five times of its level in an acute wound (Yager et al, 1996, Trengove et al, 1999). MMP-9 is the major protease that is present in the chronic venous stasis and decubitus ulcers.

The tissue inhibitor of metalloproteinase (TIMP-1) is absent from chronic wounds and is also decreased with age.

These chronic wounds also become colonized with bacteria. The bacterial colonies produce a biofilm which enables the bacteria to act as a multicellular organism. The biofilm protects the bacteria from the host immune system and all antibiotics. The bacterial biofilm gains nutrients from its own protease, which are similar to the host MMP-9. The biofilm then protects the bacteria from the host immune system and all antibiotics. Thus, in chronic wounds, the bacterial biofilm and the host both produce proteases which are responsible for the degradation of the factors responsible for wound healing.

Research has shown that silver nanoparticles (AgNPs) can be manufactured into specific shapes that show improved antibacterial properties (Pal, S., Y. K. Tak and J. M. Song, 2007, Does the antibacterial activity of silver nanoparticles depend on the shape of the nanoparticle? A study of the gram-negative bacterium *Escherichia coli*. Appl. Environ. Microbiol. 2007, 73(6):1712). The specific AgNP shapes also demonstrate improved anti-inflammatory and angiogenic properties. The specific AgNP shapes which have shown improved antibacterial, anti-inflammatory, and angiogenic properties include silver nano prisms (AgNPr), silver nano truncated triangle plates (AgNTTP), and silver nano discs (AgND). The specific AgNP shapes allow for the use of a lower concentration of silver and produce a more effective wound care treatment than other silver compositions.

The AgNTTP (silver nano truncated triangular plates) have shown the strongest antibacterial activity due to the surface $\{111\}$ facet characteristics (Wijnhoven, S. W. P., Peijnenburg, W. J. G. M., Herberts, C. A., Hagens, W. I., Oomen, A. G., Heugens, E. H. W., Roszek, B., Bisschops, J., Gosens, I., Van De Meent, D., Dekkers, S., De Jong, W. H., van Zijverden, M., Sips, A. J. A. M. and Geertsma, R. E., 2009. Nano-silver—a review of available data and knowledge gaps in human and environmental risk assessment. Nanotoxicology, 3:2, 109-138). The reactivity of the nano silver is improved by the high atom density surface $\{111\}$ facet (Hatchett, D. W. and Henry, S. 1996, Electrochemistry of sulfur adlayers on low-index faces of silver. Jl. Phys. Chem. 100:9854-9859).

Silver nanoparticles also demonstrate strong anti-fungal properties (Wright, J. B., Lam K, Hansen D., Burrell R. E., 1999, Efficacy of topical silver against fungal burn wound pathogens. Am. Jl. Infect. Control 27:344-350), anti-viral properties that inhibit HIV-1 replication (Sun, R. W., Chen R., Chung N. P., Ho C. M., Lin C. L., Che C. M. 2005. Silver nanoparticles fabricated in Hepes buffer exhibit cyto-protective activities toward HIV-1 infected cells. Chem. Commun (Camb.):5059-5061), and anti-inflammatory properties (Kirsner R. S., Orsted H., Wrught J. B. 2002. Matrix metalloproteinases in normal and impaired wound healing: a potential role of nanocrystalline silver. Wounds 13:4-12).

As noted above, elevated inflammatory mediators are responsible for chronic wounds not healing. The chronic inflammatory mediators that are most responsible for non-healing diabetic wounds include matrix metalloproteinases (specifically MMP-9), tumor necrosis factor (TNF-alpha), and interluken (IL-1 and 12). (Rayment, E. A., Upton Z., Shooter G. K., 2008, Increased matrix metalloproteinase-9 (MMP-9) activity observed in chronic wound fluid is related to the clinical severity of the ulcer. British Jl. of Derm. 158, pp 951-961). The AgNP shapes with $\{111\}$ facets suppress these proteolytic enzymes that are responsible for the non-healing chronic wounds (Wright J. B., Lam K., Buret A. G., Olson M. E., Burrell R. E., 2002, Early healing events in a porcine model of contaminated wounds: Effects of nanocrystalline silver on matrix metalloproteinases, cell apoptosis, and healing. Wound Repair Regen. 10:141-151).

As discussed above, chronic venous, lymphatic and diabetic wounds include a high bacterial load, glycoprotein biofilm, and chronic inflammatory mediators. The biofilm produced by the bacteria prevents the effectiveness of antibiotics and the host immune system against the bacteria. However, the incorporation of AgNP into a treatment area will inhibit the bacteria as well as the formation of the biofilm (Percival, S. L., Bowler P. G., Dolman J., 2007, Antimicrobial activity of silver-containing dressings on wound microorganisms using an in vitro biofilm model. Int. Wound Jl. 4:186-191).

One successful device to treat chronic wounds is described in U.S. Pat. No. 9,220,636, entitled "Sock For Treatment of Foot and Leg Wounds, Methods of Use and Manufacture," by the present inventor ("the '636 Patent"), the disclosure of which is incorporated herein in its entirety. The '636 Patent discloses embodiments of compressions stockings knit from a combination of natural wicking fibers and elastic fibers, and with AgNP including specific AgNP shapes adhered to the natural fibers. The compression stocking can be applied directly onto the wound with the natural wicking fibers with adhered AgNP coming into contact with the wound. This compression stocking design has been shown to down regulate the MMP-9 and bacterial proteases, kill the bacteria that are protected by the biofilm, and allow the epithelialization of the wound without harming the keratinocytes.

Preliminary clinical trial results of a compression stocking incorporating the features disclosed in the '636 Patent, referred to as the Vive stocking, are encouraging. Patients that had failed current standard of care treatment for lower extremity wounds were referred to a wound clinic for evaluation and treatment. After informed consent was obtained, five patients were started in a preliminary clinical trial using the Improved Sock with wool and alpaca fibers, elastic fibers for compression, and AgNP (See Table 1). The age of these five preliminary clinical trial patients with chronic wounds (five patients) and acute wounds (one patient) ranged from 58 to 87.

cal trial had failed to heal. Some of the chronic wounds treated with the Vive stocking had been present for several years. As expected, the larger chronic wounds took longer to heal. Nonetheless, all of the wounds that had been present for over one year and then treated with the Vive stocking healed in 10 to 12 weeks, and have not recurred.

The one acute preliminary clinical trial patient with acute fungal and MRSA wounds healed in 2 weeks.

The most remarkable result from the clinical trial occurred in an 87-year-old woman who presented to the hospital in septic shock with circumferential ulceration of her left leg from the knee to ankle. She had chronic venous stasis ulcers that failed treatment using compressive wrap with an Unna boot. Her initial wound cultures were positive for MRSA. Initial consultation from a general surgeon was to consider an amputation of the leg above the knee. After informed consent with the patient and her family (including a dermatologist), they elected to try the Vive stocking. The Vive stocking was changed daily at bedside and washed in regular soap and water. The patient underwent no anesthesia or surgical debri-

TABLE 1

| Patient Age | Co-morbidities | Wound Duration (months) | Wound Culture | Previous Antibiotic Treatment | Previous Compression Therapy | Wound Size ($cm^2$) | Time to heal (weeks) | Sock changed worn 24 hr/day |
|---|---|---|---|---|---|---|---|---|
| 70 | HL, TR, CS | >12 | | | Mag. | 50 | 12 | Weekly |
| 79 | EM, SM, HTN | 3 | | | SC, AC | 40 | 3 | Weekly |
| 24 | | 4 | MRSA | Clindamycin, Ciprofloxacin, TMP-SMZ | | 1 | 1 | Weekly |
| 58 | DM, HTN, CO, LY, SA | >12 | | Doxycycline, Vancomycin, Zosyn | SC, XC, SI | Entire leg | 10 | Daily |
| 87 | SS, VSI, ARF | Acute | MRSA | Doxycycline | | Entire leg | 14 | Daily |

Abbreviations used in table:

Comorbidities: ARF—acute renal failure; CO—COPD; DM—diabetes; EM—emphysema; HL—hyperlipidemia; HTN—hypertension; LY—lymphedema; SA—sleep apnea; SM—smoker; SS—septic shock; TR—trauma; VSI—venous stasis insufficiency Previous Compression Therapy: AC—ACell MatriStem®; CS—Kendal T.E.D.® hose; DY—Johnson & Johnson DYNA-FLEX®; Mag-Molnlycke Mepilex® Ag; SC—Johnson & Johnson Silvercell®; SI—Silver sulfadiazine; UN—Unna boot; VAC—KCI wound V.A.C.®

In all cases, the pain decreased. The only complication occurred in the 58 year old patient, whose wound healed uneventfully, despite a dorsal ankle ulcer from sock fold.

The chronic wound patients' previous treatment had included compression therapy using Kendal T.E.D™ compression stockings, Johnson & Johnson DynaFlex® compression wraps, and Unna compression boot. One patient had a wound treated with a KCI wound V.A.C. Wound dressings included silver alginate such as Johnson & Johnson Silvercel®, and Molnlycke Mepilex® Ag. Treatment with skin graft substitutes included ACell MatriStem®, and Organogenesis Apligraf®. Prior therapies for the chronic wound patients enrolled in the preliminary clinical trial included several months of a broad spectrum of oral and intravenous antibiotics.

Despite aggressive standard of care treatment, all of the patients' wounds that were enrolled in the preliminary clinidement. After a week of rapid improvement the patient was discharged to a skilled nursing facility. While at the skilled nursing facility the wound care nurse resumed traditional wound dressing including graduated compression. After two weeks the wound became significantly worse. The Vive stocking was then reapplied and changed every 2 to 3 days depending on the amount of drainage. After 14 weeks the treated leg wounds completely healed. The patient subsequently wore the Vive stocking daily without any swelling or sign of skin breakdown. No ulcers had reoccurred two months after healing.

There are currently many medical and non-medical wound care products on the market that contain silver. These silver wound care dressings have become a standard therapy for patient wound care. The antibacterial properties of silver are well known but the side effects of systemic absorption of the silver have been the concern of recent studies. A recent animal study using two well-known commercially available silver dressings shows that silver was detected by plasma mass-spectroscopy in all analyzed organs and tissue samples of the animals using the wound dressings. Organ concentration levels of silver were detected at the highest levels in the nano crystalline silver dressings and were also detected from the silver sulphate foam. The highest silver concentrations were detected in the spleen, kidney and liver. (Pfurtscheller, K., Petnehazy, T., Goessler, W., Bubalo, V., Kamolz, L., Trop, M., Transdermal uptake and organ distribution of silver from two different wound dressings in rats after a burn trauma. Wound Rep. Reg. 22:654-659.) As noted in the Pfurtscheller et al. study, silver leaching can be detrimental to both the patient and the environment.

The Vive stocking was independently tested to determine if any silver would leach out of the fibers. Independent testing at Bucknell University, including an atomic absorption (AA) spectrometer flame test and a zone of inhibition (ZOI) antibacterial test, demonstrated that the Vive stocking did not leach silver even after being washed in soap and water.

Atomic Absorption (AA) Spectrometer Flame Test

This test was advised by Monica Hoover, Director of Environmental Engineering and Science Laboratory, Bucknell University.

Methods

A standard curve was made using a multi-elemental standard solution prepared for the Aurora Al 1200 Flame Test. The standard curve quantifies the amount of silver within a solution from a peak height provided by the spectrometer. Three samples were made with 10 mL of water including the following:

Product A—1 cm by 1 cm piece of a standard silver alginate dressing (SilverCel®)

Product B—AgNP in solution (1 mL of the AgNP not bonded to the stocking)

Product C—1 cm by 1 cm piece of Vive stocking.

Product A, Product B, and Product C were each combined with 10 mL of water and placed in a separate test tube. Each test tube was shaken for 10 minutes and a sample was sent through the AA spectrometer. In other words, Product A was placed in a test tube with 10 mL of water and shaken for 10 minutes. Then the piece of standard silver alginate dressing was removed from the test tube and the remaining solution was sent through the AA spectrometer. Similarly, Product C was placed in a test tube with 10 mL of water and shaken for 10 minutes. Then the piece of Vive stocking was removed from the sample and the remaining solution was sent through the AA spectrometer. As to Product B, 1 mL of AgNP were added to 10 mL of water and the solution was shaken. Nothing was removed from the solution of Sample C before sending the solution to the AA spectrometer.

After the preliminary testing above, it was determined that the original 10 mL solutions of Product A (silver alginate dressing) and Product B (silver solution) required a ten times dilution to be within the range of concentrations produced by the standard curve. Product C (Vive stocking) did not leach silver upon preliminary testing, so the solution was not diluted. Table 2 shows the results from the AA spectrometer flame test when the test was performed on Product A with ten times dilution, Product B with ten times dilution, and Product C.

Results:

TABLE 2

| Samples | Pk Height | Result ppm |
| --- | --- | --- |
| A: SilverCel ® (10×) | 0.166 | 19.723 |
| B: AgNP in solution (10×) | 0.220 | 27.584 |
| A: SilverCel ® (10×) | 0.199 | 28.16 |
| B: AgNP in solution (10×) | 0.16 | 21.86 |
| C: Vive (1×) | 0.004 | 0 |
| C: Vive 1 hr wash | 0.011 | 0 |

Each of the tests for Product A and Product B were run twice, as indicated by "A" and "B" in the Table 2. As shown in Table 2, Product B (silver solution) produced a detectable amount of silver, making Product B (silver solution) important as a positive control. Product B (silver solution) is the same solution used to coat the wool within the Vive stocking. Also as shown in Table 2, Product C (the Vive stocking) did not leach any silver after 10 seconds of shaking. It was then placed on a shaker for an hour with soap to simulate a wash cycle. Product C (the Vive stocking) did not leach after this period.

Conclusions

The Vive stocking did not leach silver to the detectable limits of the AA spectrometer Flame Test. Product A (silver alginate dressing) leached 28 ppm of silver into the water after 10 seconds of shaking.

Zone of Inhibition (ZOI) Antibacterial Test

This test was advised by Dr. Marie Pizzorno, Professor of Biology, Bucknell University.

The Vive stocking demonstrated safety to the patient and the environment by not leaching silver. The next step was to demonstrate that the Vive stocking had equivalent antibacterial activity as Product A (silver alginate dressing) that leached silver. The test that best replicates the actual usage of the Vive stocking is a zone of inhibition test. In this test the stocking is applied directly to an agar plate. The agar best replicates the true environment of the stocking in direct contact with a moist wound.

Methods

Thirteen nutrient agar plates were prepared with 50 µL of *Staphylococcus epidermidis* (staph). Staph was used for testing because it is a gram-positive bacterium that is commonly present in hospitals. It is a common cause for infections in patients. Two samples (one silver alginate dressing and one Vive stocking) were cut approximately 1" in diameter. The samples were glued to cardboard to prevent rolling. The samples were placed carefully on top of the bed of Staph. The plates were incubated for 48 hours at 37° C. To calculate the ZOI of each sample, the dressing widths were subtracted from the zone widths (Landry et al., 2009). This was repeated in duplicate perpendicular directions (Landry et al., 2009).

Results

FIG. 1 is a representative photo of a sample, reproduced in line drawing format. A sample plate system 100 includes a plate 101. A silver alginate dressing sample 102 and a Vive stocking sample 103 are disposed on the plate 101. Staph 104 is identified by the grey region. The silver alginate dressing sample 102 has a zone of inhibition 105 and the Vive stocking sample 103 has a zone of inhibition 106.

As can be seen in FIG. 1, a bed of staph covers the entirety of the plate except for the silver alginate zone of inhibition 105 and the Vive stocking zone of inhibition 106. The silver alginate zone of inhibition 105 and the Vive stocking zone of inhibition 106 represent areas of limited antibacterial growth of staph. Thus, a sample with a larger and clearer zone of inhibition is more antibacterial.

Conclusions

The Vive stocking and the silver alginate wound dressing both limit the growth of *Staphylococcus epidermidis* ("staph"), as indicated by a clear ring of negated bacteria in each sample. For example, as shown in FIG. 1, the silver alginate zone of inhibition 105 and the Vive stocking zone of inhibition 106 represent areas of limited antibacterial growth of staph. The zone of inhibition of the Vive stocking was consistently equal to or greater than the zone of inhibition of the silver alginate dressing.

Research studies have also shown that wound healing can be enhanced by application of electrical currents to the wounds. The use of electrical field energy applied to chronic wounds demonstrates improved blood flow, increased angiogenesis and reduced wound necrosis in patients with chronic venous leg ulcers. A meta-analysis of clinical trials has shown electrical stimulation effectively promotes wound closure. (Gardner, S. E., Frantz, R. A., Schmidt, F. L., 1999, Effect of electrical stimulation on chronic wound healing: a meta-analysis. Wound Rep. Reg. 7:495-503; Kawasaki, L, Mushahwar, V. K., Ho, C., Dukelow, S. P., Chan, L. L. H., Chan, K. M., 2013, The mechanisms and evidence of efficacy of electrical stimulation for healing of pressure ulcer: a systematic review. Wound Rep. Reg. 22:161-173. Kloth, L. C., Electrical Stimulation Technologies for Wound Healing. Adv Wound Care (New Rochelle). 2014 Feb. 1; 3(2): 81-90.)

The Wound Healing Society (WHS) published an updated position paper for wound healing guidelines in 2014. Guideline #7.2.3 states there is Level 1 evidence that "Electrical stimulation accelerates wound closure and the proportions of wounds that heal in RCTs and prospective and retrospective cohort studies". (Braun, L., Kim, P., Margolis, D., Peters, E., Lavery, L., What's new in the literature: An update of new research since the original WHS diabetic foot ulcer guidelines in 2006. Wound Rep. Reg. 22:594-604.)

Multilayer compression socks on the market today simply use a two layer sock kit (traditional kit). This traditional kit includes two layers of sock over the foot, ankle and calf. The bulk of the two layers of sock over the foot makes wearing regular shoes with the traditional kit difficult. Also, the two layers of sock over the ankle add pressure to the ankle which has caused ulceration. Due to the bulk and compression, the traditional kit is challenging for patients put on their calf, ankle, and foot. For these reasons, patients tend to not be compliant with wearing both sock layers of the traditional kit. When patients are not compliant, reoccurrence of ulcers is common. Therefore, using the traditional kit places patients at risk of developing iatrogenic ankle ulcers.

Thus, there is a need for a wound treatment device that provides the benefits of compression, incorporates AgNP, and produces an electrical current while minimizing the drawbacks of silver leaching, bulkiness, and iatrogenic ankle ulcers to achieve increased compliance and wound healing.

SUMMARY

Embodiments of a compression stocking disclosed herein provide improved healing of chronic wounds. In some embodiments, an apparatus includes a tubular body configured to be disposed around an extremity of a patient. The tubular body is also configured to apply compression to the extremity. The tubular body includes a treatment area having a first filament and a second filament. Both the first filament and the second filament are disposed to engage the surface of the extremity. The first filament includes AgNP in a concentration effective to promote healing of a wound on the surface of the extremity. The second filament includes a metal having a composition that forms a galvanic couple with silver. The first filament and the second filament are arranged in the tubular body, and the AgNP and metal are arranged in the filaments, such that the AgNP and metal form galvanic couples across at least a portion of the treatment area when in the presence of a fluid in the wound of the extremity that produce an electric current in an amount effective to further promote healing of the wound.

DETAILED DESCRIPTION

The disclosed compression stockings may be used for patients with ulcerations from arterial, venous and lymphatic insufficiency, diabetes, and for other people as well. The disclosed compression stockings may have a compression function, with graduated compression from the foot up through the calf. The compression stockings may also include AgNP that provides anti-microbial, anti-inflammatory, and angiogenic functions. The compression stockings may also include, in combination with the AgNP, one or more other metals that form galvanic couples with the AgNP to provide electric currents that improve wound healing.

Figure 1:
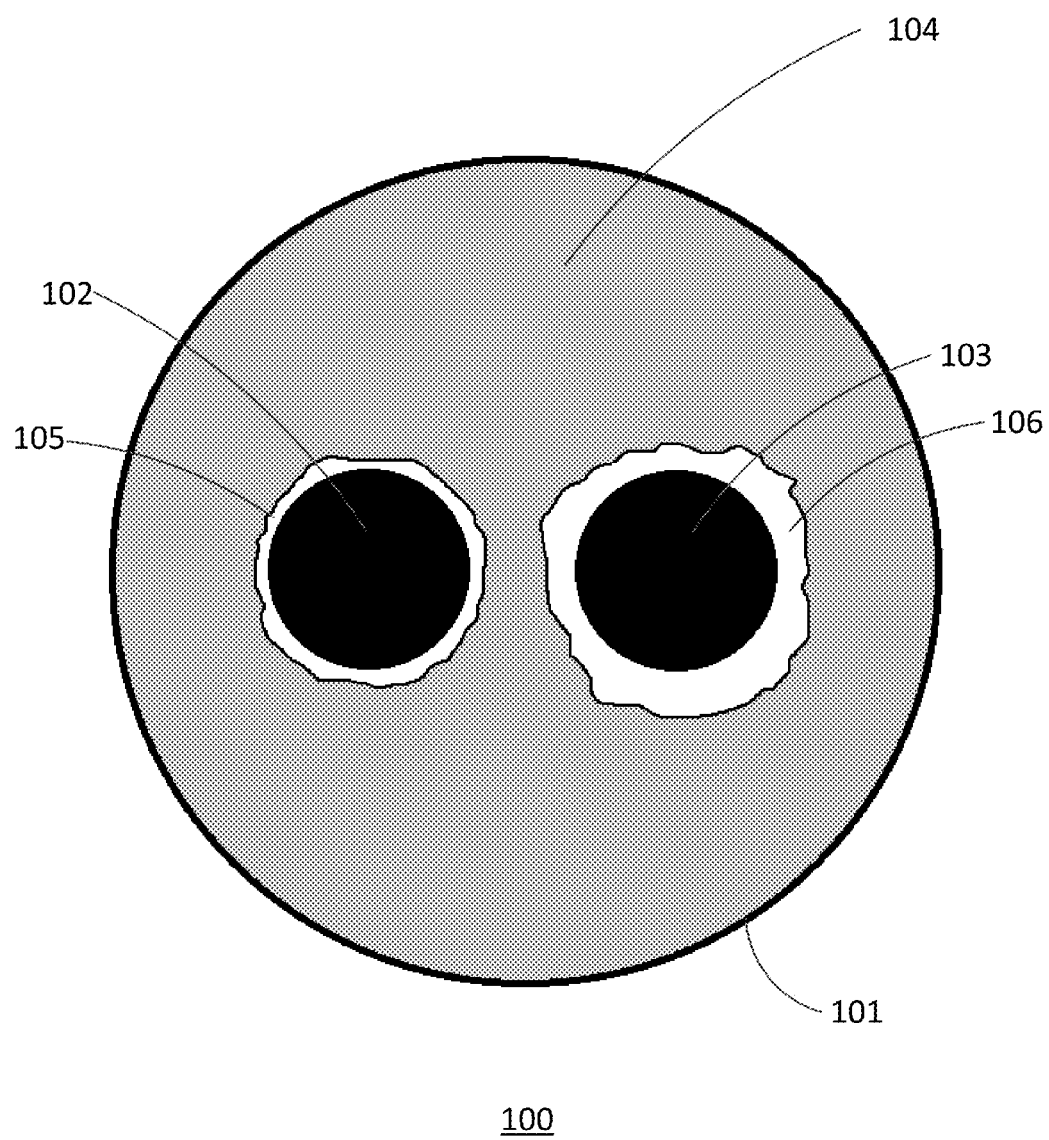
FIG. 1 is a representative photo of a sample from a zone of inhibition test reproduced in line drawing format.
Figure 2:
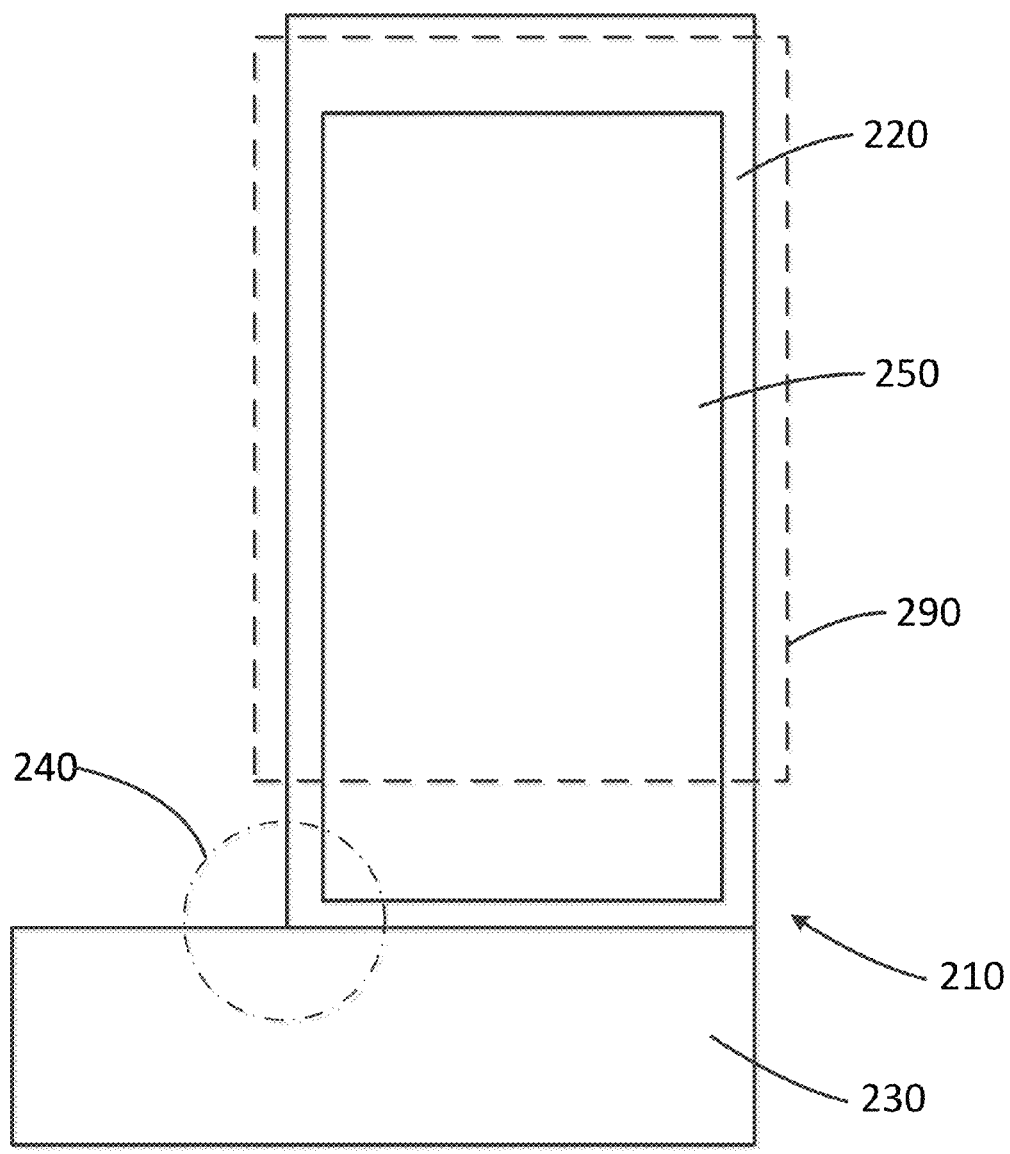
FIG. 2 is a schematic illustration of a compression stocking according to an embodiment.

A compression treatment stocking system according to a first embodiment is illustrated schematically in FIG. 2. The compression treatment stocking system 200 includes a tubular body 210 (i.e., a first tubular body). The tubular body 210 can include a leg portion 220 and a foot portion 230, and can form a sock or stocking. The leg portion 220 can be configured to be disposed around a lower extremity, e.g. a lower leg, of a patient and to apply compression to a compression treatment area of the extremity. For example, the leg portion 220 can be configured to be disposed from an ankle to a knee of a patient. The foot portion 230 can be configured to conform to the patient's foot and to apply compression to at least a portion of the foot. The leg portion 220 and/or foot portion 230 may also include one or more electrical treatment areas 250, in which at least some constituent filaments include AgNP, and in which at least some other constituent filaments are composed of or include other metals that can form a galvanic couple with the AgNP. The galvanic couple can provide electrical stimulation to a wound surface and promote epithelial growth. The electrical treatment area 250 can be contained within the compression treatment area, can overlap with the compression treatment area, or can be distinct from the compression treatment area. The tubular body 210 can also include a pressure relieving ankle section 240. Optionally, the compression treatment stocking system 200 may include a separate, supplemental compression sleeve 290, to provide additional compression to the lower extremity. The compression sleeve 290 can be configured to allow the patient to vary the compression over the leg area between a first compression profile (applied by the tubular body 210 without the compression sleeve 290) and a second compression profile (applied by the tubular body 210 in combination with the compression sleeve 290) as instructed by a physician.

The tubular body 210 may be formed with two material components, including: an elastic component and a wicking component. The elastic component provides a compression function. The wicking component maintains a homeostatic wound environment by wicking away from the skin and wound the inflammatory exudate, the bacteria and biofilm, and debriding necrotic tissue from the wound while maintaining a moist wound environment. The wicking component provides a comfortable and pleasant skin-contacting surface for the wearer. The elastic component may be formed of filaments (also referred to herein as fibers or yarns) of an elastic material such as latex or latex-free elastomers, spandex, various rubbers, texturized polyester, and/or nylon. The wicking component may be formed of filaments of wool, such as sheep's wool, cashmere or mohair from goats, qiviut from muskoxen, angora from rabbits, and wool from camelids such as vicuna, guanaco, alpaca, and llama. Wools with fine fibers, such as Merino and alpaca, are preferred. Alpaca wool has been shown to have better wicking ability and compressibility (provides more cushion), to be softer, and to be more durable than other wools (Liu, X., Wang, L. and Wang, X., 2004, Resistance to compression behavior of alpaca and wool, Textile Research Journal, vol. 74, no. 3 pp. 265-270).

In one embodiment, the tubular body 210 may be knit from a yarn formed with a 50/50 blend of alpaca and merino wools. The fibers of the yarn can be about 18.5 microns in diameter, and the fibers can be spun into a yarn with dimensions of 1/44 NM (single yarn, 44 number metric in diameter). The fibers can be spun in a covering arrangement over an elastic core, so that the wool, not the elastic, is in contact with the skin and the wound. In one embodiment, a double-covered elastic yarn is used to achieve a high degree of compression. The tubular body 210 may be fabricated using conventional processes, such as warp and/or weft knitting.

The leg portion 220 of the tubular body 210 provides graduated compression from the ankle through at least a portion of the calf. The compression is greater at the ankle and gradually decreases up to the calf. In one embodiment, for example, the compression ranges from about 20 to about 24 mm Hg at the ankle, and decreases to about 15 to about 18 mm Hg at the top of the calf, which for some patients may be an appropriate upper limit for continuous wear. Studies of compression in this range show increased circulation up to 40%. In this range, the compression prevents pooling of blood in the ankle and calf and does not inhibit microcirculation in the skin. In other embodiments, the compression ranges from about 20 mm Hg at the ankle to about 15 mm Hg at the top of the calf. Other lower ranges may be appropriate for some patients. For example, patients who experience poor atrial circulation or who cannot tolerate a higher level of compression may prefer an embodiment with a reduced compression range. The tubular body 210 can apply compression that is gentle enough that the tubular body 210 can be worn 24 hours a day to provide continuous compression and continuous wound treatment. Additionally, clinical studies have shown that regular daily wearing of the tubular body 210 after the wound has healed prevents reoccurrence of wounds. The compression amounts can be confirmed on a Hatra type apparatus, such as a CMD-100.

As noted above, the compression treatment stocking system 200 can include a separate compression sleeve (i.e., a second tubular body) 290. The compression sleeve 290 can be worn over the tubular body 210. The compression sleeve 290 can provide additional compression over an area of the ankle and/or calf requiring compression therapy while not increasing the bulk of the compression treatment stocking system 200 around the foot of the user. Because the compression treatment stocking system 200 includes only one layer on the user's foot, the user can comfortably wear regular shoes while using the compression treatment stocking system 200. As a result, user compliance increases.

Another reason the compression treatment stocking system 200 encourages increased patient compliance is that the compression sleeve 290 is also much easier to don and doff than compression stocking systems that include two compression stockings layered into a two-layer stocking system. The user can first put on the tubular body 210 which will apply compression to the patient's ankle and calf. With the tubular body 210 in place, the user can put on the compression sleeve 290 over the tubular body 210. Because the patient's ankle and calf are already under compression from the tubular body 210, the compression sleeve 290 is easier to position over the ankle and calf. Additionally, the compression sleeve 290 can be worn only during certain periods while the tubular body 210 provides continuous compression therapy depending on doctor recommendations. For example, the compression sleeve 290 can be worn during most waking hours of the day and removed at night to comply with doctor-recommended microcirculation requirements. Additionally, the user can easily remove the compression treatment stocking system 200 to wash the leg daily. Also, the user is not required to visit a health care provider for reapplication of the compression treatment stocking system 200 because sterility is not necessary and the compression treatment stocking system 200 is easily donned by the user. As a result of these described features of the tubular body 210 and compression sleeve 290 combination, no patients in an initial trial study had recurrent ulceration.

Similar to the tubular body 210, the compression sleeve 290 may also be formed with two material components, including: an elastic component and a wicking component. The elastic component provides a compression function. The wicking component assists the tubular body 210 in maintaining a homeostatic wound environment by wicking away inflammatory exudate, bacteria and/or biofilm from the tubular body 210. The elastic component may be formed of filaments (also referred to herein as fibers or yarns) of an elastic material such as latex or latex-free elastomers, spandex, various rubbers, texturized polyester, and/or nylon. The wicking component may be formed of filaments of wool, such as sheep's wool, cashmere or mohair from goats, qiviut from muskoxen, angora from rabbits, and wool from camelids such as vicuna, guanaco, alpaca, and llama. Wools with fine fibers, such as Merino and alpaca, are preferred. Alpaca wool has been shown to have better wicking ability and compressibility (provides more cushion), to be softer, and to be more durable than other wools (Liu, X., Wang, L. and Wang, X., 2004, Resistance to compression behavior of alpaca and wool, Textile Research Journal, vol. 74, no. 3 pp. 265-270).

Like the tubular body 210, in one embodiment, the compression sleeve 290 may be knit from a yarn formed with a 50/50 blend of alpaca and merino wools. The fibers of the yarn can be about 18.5 microns in diameter, and the fibers can be spun into a yarn with dimensions of 1/44 NM (single yarn, 44 number metric in diameter). The fibers can be spun in a covering arrangement over an elastic core, so that the wool, not the elastic, is in contact with the skin and the wound. In one embodiment, a double-covered elastic yarn is used to achieve a high degree of compression. The compression sleeve 290 may be fabricated using conventional processes, such as warp and/or weft knitting.

For optimal therapy, the combined compression of the compression treatment stocking system 200 is graduated from about 40 to about 30 mm Hg, with 40 mm Hg compression at the ankle and 30 mm Hg at the top of the calf. Said another way, the tubular body 210 applies a first compression profile to the ankle and calf of the user and the compression sleeve 290 can apply a second compression profile to the ankle and calf of the user. The combined compression profile of the first compression profile and the second compression profile can be a gradient ranging from 30-40 mm Hg, decreasing from 40 mm Hg compression at the ankle to 30 mm Hg at the top of the calf. In some embodiments, the first compression profile and the second compression profile both decrease in compression from the ankle to the top of the calf. For example, the first compression profile can range from 24 mm Hg at the ankle decreasing to 18 mm Hg at the top of the calf. The addition of the compression sleeve 290 to the tubular body 210 can create a combined compression profile ranging from 40 mm Hg at the ankle decreasing to 30 mm Hg at the top of the calf.

In other embodiments, the first compression profile can range from about 20 mm Hg at the ankle to about 15 mm Hg at the top of the calf, and the second compression profile can also range from about 20 mm Hg at the angle to about 15 mm Hg at the top of the calf. In combination, the combined compression profile ranges from about 40 mm Hg at the ankle to about 30 mm Hg at the top of the calf. In other embodiments, one of the first compression profile or the second compression profile can be constant while the other decreases in compression from the ankle to the top of the calf. In embodiments that do not include a compression sleeve 290, the tubular body 210 can have a compression profile of a gradient ranging from 30-40 mm Hg, decreasing from 40 mm Hg compression at the ankle to 30 mm Hg at the top of the calf. Additionally, while users with healthy arterial circulation may experience the best results with a compression range of about 40 mm Hg at the ankle to about 30 mm Hg at the top of the calf or knee, users who experience poor arterial circulation or who cannot tolerate as much compression may prefer a low compression range from the ankle to the top of the calf or knee, which can be achieved by only using the tubular body 210 or by using a tubular body 210 and a compression sleeve 290 with reduced compression profiles.

The tubular body 210 and the compression sleeve 290 can be sized to fit a particular user and achieve a particular compression profile on a particular user. For example, Table 3 shows a sizing guide based on standards set by the National Association of Hosiery Manufacturing (NAHM) that can be used to determine the appropriate size of the tubular body 210 and the compression sleeve 290 for a particular user based on the foot, ankle, and calf size of the user.

portion size D and a leg portion size 5, a foot portion size B and a leg portion size 2, or a foot portion size C and a leg portion size 5, depending on the shape of the user. Additionally, although standard foot portion sizes A, B, C, D, E and standard leg portion sizes 1, 2, 3, 4, 5 are described in Table 3, the tubular body 210 can be customized such that the foot portion 230 and/or the leg portion 220 are between sizes described in Table 3 or are larger or smaller than sizes described in Table 3. Additionally, the tubular body 210 can be formed with any suitable length such that the desired compression profile is applied to the user from the ankle to the top of the calf. The appropriate size for the compression sleeve 290 can be determined using Table 3 similarly as used to determine the appropriate size for the leg portion 220 of the tubular body 210.

The pressure relieving ankle section 240 is a special pressure relieving area over the dorsum of the ankle. The pressure relieving ankle section 240 will address the problem identified above experienced by the patient with the iatrogenic dorsal ankle ulcer from the sock fold. The tubular body 210 can include a special weave with decreased compression between the leg portion 220 and the foot portion 230 to prevent increased pressure on the dorsum of the foot. The decreased pressure in ankle section 240 minimizes the risk of ulceration on the front of the ankle. Additionally, in embodiments where the compression treatment stock system 200 includes both the tubular body 210 and the compression sleeve 290, the combination of the tubular body 210 and the compression sleeve 290 can achieve a desired compression profile (e.g., a 30-40 mm Hg gradient) over the ankle and/or calf without unnecessarily increasing compression on the dorsum of the ankle. This reduces the risk of ulceration compared to traditional single layer 30-40 mm Hg compression stockings or two-layer 30-40 mm Hg compression stockings, which both create increased stress over the dorsum of the ankle.

As noted above, leg portion 220 and/or foot portion 230 of the tubular body 210 may also include one or more electrical treatment areas 250. Within at least the electrical treatment area 250, at least a portion of the constituent yarns or filaments are treated with AgNP. The AgNP may be incorporated into the yarns or filaments in the electrical treatment area 250

TABLE 3

| Sock Size | Shoe Size (Men) | Shoe Size (Women) | Foot Circumference (cm) | Foot Portion Size | Ankle Circumference (cm) | Calf Circumference (cm) | Ankle Foot Circumference (cm) | Leg Portion (Calf) Size |
|---|---|---|---|---|---|---|---|---|
| 16 | 16.5-18 | | 32 | E | 29 | 45 | 42.5 | 5 |
| 13 | 12-12.5 | | 27 | D | 26 | 39 | 37 | 4 |
| 11 | 8.5-9 | 9.5-10.5 | 25 | C | 23 | 36 | 33.5 | 3 |
| 10 | 6-6.5 | 6.5-7.5 | 23 | B | 21 | 33 | 31 | 2 |
| 9 | 3-4 | 4-5 | 21 | A | 19 | 29 | | 1 |

As shown in Table 3, the foot portion 230 of the tubular body 210 can have a size identified by a letter (e.g., A, B, C, D, E) and the leg portion 220 of the tubular body 210 can have a size identified by a number (e.g., 1, 2, 3, 4). A user's (e.g., a patient's) foot portion 230 size can be determined using the user's typical sock size, shoe size, and/or foot circumference. Similarly, a user's leg portion 220 size can be determined using the user's ankle circumference, calf circumference, and/or ankle foot circumference. The tubular body 210 can be manufactured such that it is sized according to any combination of foot portion 230 size and leg portion 220 size. For example, the tubular body 210 can be formed to have a foot so as to be durable and machine washable. The AgNP can include AgNP shaped as truncated triangular plates (AgNTTP) (i.e., triangular plates with the corners rounded off), prisms (AgNPr) such as triangular prisms (AgNTP), and discs (AgND). In some embodiments, at least 30% of the mass of the AgNP attached to the fibers have an AgNTTP, AgNPr, or AgND shape. In some embodiments, the AgNP can include mixtures of two or more of the different types of shapes. In some embodiments, at least 30% of the mass of the AgNP attached to the fibers have a shape where the length of the two principal axes of the nanoparticle are more than three times greater than the length of the third principal axis of the nanoparticle and where the length of the third principal axis is less than 50 nm. In some embodiments, the AgNP (e.g., AgNTTP, AgNPr, or AgND) are combined in a ratio to maximize the anti-bacterial, anti-inflammatory, and angiogenic properties. In some embodiments, the AgNP contribute less than 0.1% of the weight of the tubular body 210. AgNP are reduced to the specified AgNP shapes through a reduction chemical reaction.

The AgNP is evenly applied to the natural fibers. In one embodiment, this is performed by drawing alpaca and merino wool yarn through a silver suspension. By maintaining a constant speed of the yarn drawn through the silver solution, a specific concentration of AgNP is deposited on the fiber. The natural fiber evenly absorbs the AgNP as the fiber is drawn through the silver bath. The yarn is rewound on a spool and dried before being knitted into the tubular body 210 (e.g., a stocking). This process works with both dyed and non-dyed natural fibers. Alternatively, the AgNP can be sprayed onto the tubular body 210 or to the natural fibers before knitting the tubular body 210 in an even distribution.

The AgNP are bonded to the thiol groups on the natural fibers through a strong metal-sulfur covalent bond. The bond is created via Van der Waals interactions. The silver-sulfur bond is 217 kJ mol$^{-1}$ (Longo, A., Carotenuto, G., Palomba, M., De Nicola, S., Dependence of optical and microstructure properties of thiol-capped silver nanoparticles embedded in polymeric matrix. Polymers (2011) 3:1795). Additionally or alternatively, it may be that some or all of the AgNP are coupled to the natural fibers by an electrostatic bond. With the electrostatic potential of the yarn or filament positive and the electrostatic potential of the silver negative, a strong and durable electrostatic bond can be created (Tang, B., J Wang, S. Xu, T Afrin, W. Xu, L. Sun, X. Wang, 2011, Application of anisotropic silver nanoparticles: multi-functionalization of wool fabric. J. of Colloid and Interface Science 356 (2011) 513-518). In other embodiments, the AgNP may be bonded to a synthetic fiber which, when knitted with the wool fibers, will provide the same function.

Within at least the electrical treatment area 250, at least a portion of the constituent yarns or filaments may be formed from, incorporate, and/or be treated with one or more metals other than silver (e.g., copper or zinc). The non-silver metal(s) can form a galvanic couple with the AgNP in other yarns or filaments in the electrical treatment area 250. An electrical cell is created within the electrical treatment area 250 through the potential difference of two half cells. The potential difference is created by the ability of electrons to flow from one half cell to another through a redox reaction. In the electrical treatment area 250, a redox reaction occurs when electrons are transferred from an anode (e.g., copper, zinc or other metal) to a cathode (e.g., AgNP) through a salt bridge.

Standard cell potential=Standard reduction potential of the cathode+Standard reduction potential of the anode $Cu(s)+2Ag^+ \rightarrow Cu^{2+}(aq)+2Ag(s)$ $E^0{}_{cell}=E^0{}_{cathode}-E^0{}_{anode}$ $E^0{}_{cell}$=0.800 V+0.340 V Reduction Half Reaction:
 copper=0.340 V
 zinc=−0.763 V
 silver=0.800 V
Cell Potential:
 copper and silver cell potential=1.140 V
 zinc and silver cell potential=0.037 V The AgNTTP shapes have increased ionic off rate compared to typical nano silver. The higher ionic off rate of the AgNTTP shapes allows the electrochemical cell in the sock to generate an improved galvanic reaction with less silver. The decreased silver minimizes the impact of leaching of the silver on both the wearer and the environment. The other disclosed AgNP shapes may also provide increased ionic off rates.

Figure 3:
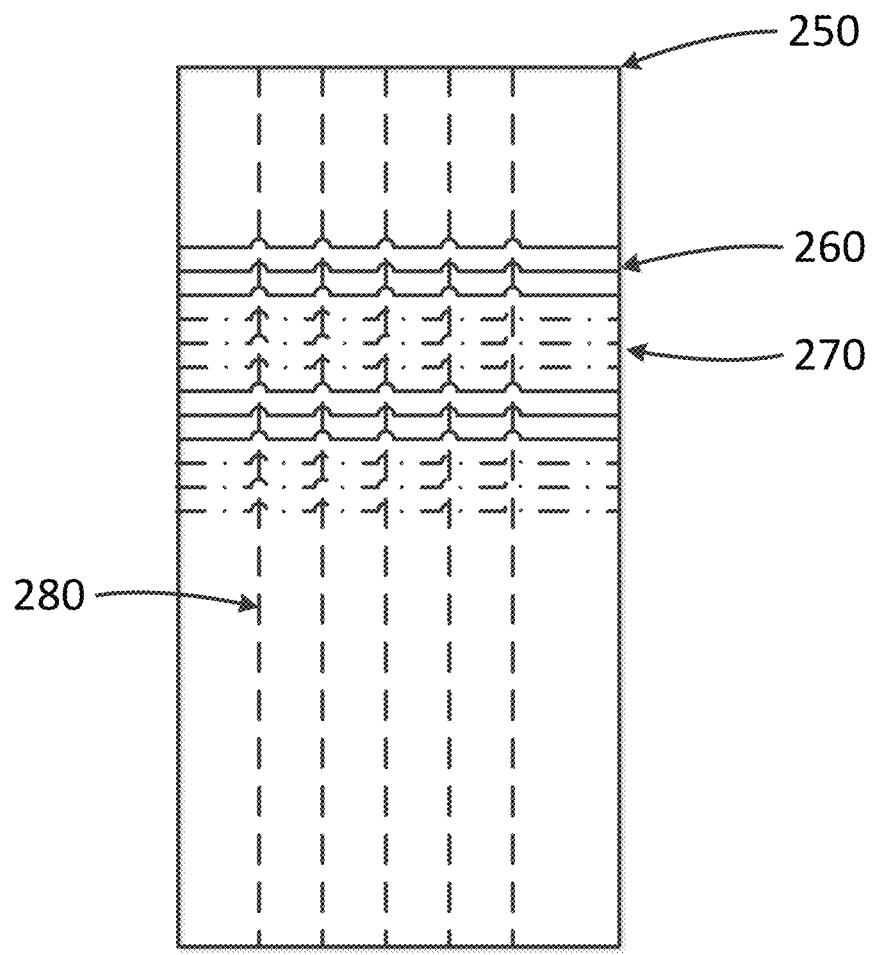
FIG. 3 is a schematic illustration of an electrical treatment area of the compression stocking of FIG. 1.

FIG. 3 is a schematic illustration of the orientation of electrically-active fibers of the electrical treatment area 250. The electrical treatment area 250 includes non-treated fibers 260, treated fibers 270, and plating yarn 280. The plating yarn 280 runs longitudinally through the electrical treatment area 250 and can run longitudinally through the entire tubular body 210. The non-treated fibers 260 and the treated fibers 270 run perpendicularly to the plating yarn 280.

The plating yarn 280 can be coated with copper, zinc, or another metal that will oxidize to become an anode of an electrochemical cell. In other embodiments, metal in the form of particles can be incorporated into the plating yarn 280. The plating yarn 280 can be formed of, for example, a polymer. The polymer can be, for example, nylon. The anode is the electron source that reduces the silver ions of the electrochemical cell. The non-treated fibers 260 and the treated fibers 270 can be natural fibers of, for example, silk or wool. For example, the non-treated fibers 260 and the treated fibers 270 can include sheep's wool, cashmere or mohair from goats, qiviut from muskoxen, angora from rabbits, and wool from camelids such as vicuna, guanaco, alpaca, and llama. Wools with fine fibers, such as Merino and alpaca, are preferred. The treated fibers 270 are treated with AgNP such that the treated fibers 270 will become a cathode of the electrochemical cell. The AgNP are bonded to the treated fibers 270 by a covalent thiol bond. For example, a covalent thiol bond can be formed between the sulfur group of the wool and/or alpaca fibers and the AgNP.

An electrical stimulation feature is activated when the electrical treatment area 250 is exposed to the fluid of an open wound. Without wound fluid, no galvanic field is generated. The non-treated fibers 260 and saline of the wound can create a salt bridge that completes an electrical circuit between the cathode (i.e., the treated fibers 270) and the anode (i.e., the plating yarn 280) of the electrochemical cell. Without a salt bridge, an electrical current cannot be developed. For example, a stocking that incorporates all of the metal particles on the same fiber is essentially combining the anode and the cathode. This structure cannot utilize a salt bridge between the anode and cathode and therefore cannot generate an electrical current or create an electrochemical cell. To generate electricity, a distance is needed between the anode (i.e., the plating yarn 280) and cathode (i.e., the treated fibers 270). This distance can be varied. For example, the distance can be within a range from about 1 mm to about 10 mm.

The activated electrochemical cell of one embodiment of the electrical treatment area 250 of the tubular body 210 generates 20 to 60 mV of electricity, as measured by, for example, a voltmeter, while it is exposed to the saline of the open wound. The electrical current generated by the electrical treatment area 250 can be modulated by varying several factors, including the number of courses of yarn including treated fibers 270, the number of courses of yarn including non-treated fibers 260, the concentration of the anode metal particles on the plating yarn 280, and the concentration of the cathode metal particles on the yarn including treated fibers 270. For example, in other embodiments, the galvanic couple can produce an electric voltage of about 10 mV or greater than 10 mV.

Figure 4:
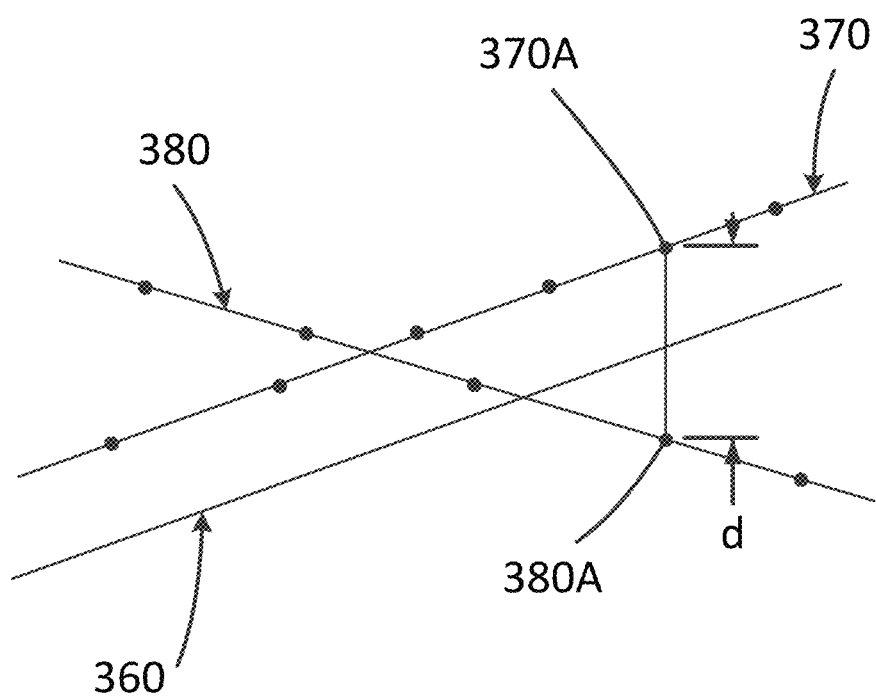
FIG. 4 is a microschematic illustration of electrically-active fibers according to an embodiment.

FIG. 4 is a microschematic of electrically-active fibers according to an embodiment. The fiber system 300 includes a non-treated fiber 360, a treated fiber 370, and plating yarn 380. The non-treated fiber 360, treated fiber 370, and plating yarn 380 can be the same as or similar to the non-treated fibers 260, the treated fibers 270, and the plating yarn 280 described above. The treated fiber 370 includes silver nanoparticles, such as silver nanoparticle 370A. The plating yarn 380 includes nanoparticles of other metals (e.g., copper or zinc), such as anode nanoparticle 380A. The silver nanoparticle 370A and the anode nanoparticle 380A are separated by a distance d. The non-treated fiber 360 is disposed between the silver nanoparticle 370A and the anode nanoparticle 380A. The combination of the silver nanoparticle 370A, the anode nanoparticle 380A, and the non-treated fiber 360 of the fiber system 300 with wound saline (not shown) forms an electrochemical cell.

When the fiber system 300 is exposed to the saline fluid of a wound, a salt bridge is created between the anode nanoparticle 380A and the silver nanoparticle 370A (i.e., the cathode). The salt bridge is created by the non-treated fiber 360 and saline of the wound. The salt bridge completes the electrochemical cell and electrons flow between the anode and cathode. The distance d can range from, for example, between about 1 mm and about 10 mm.

Figure 5:
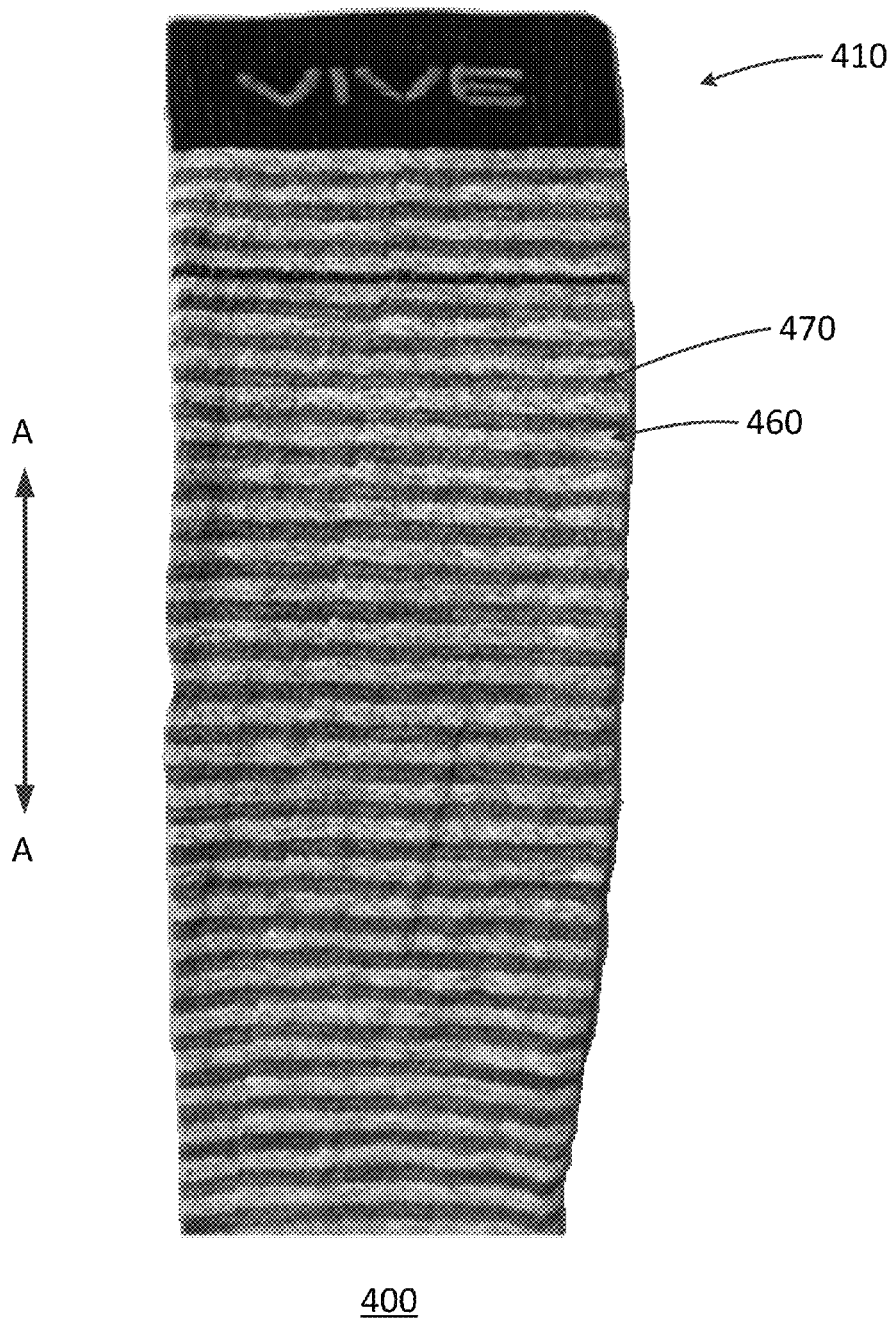
FIG. 5 is a photographic representation of a portion of a compression treatment stocking system according to an embodiment.

FIG. 5 is a photographic representation of a portion of a compression treatment stocking system according to an embodiment. The compression treatment stocking system 400 includes a tubular body 410. The tubular body 410 includes plating yarns (not shown), treated fibers 470, and non-treated fibers 460. The non-treated fibers 460, treated fibers 470, and plating yarns can be the same as or similar to the non-treated fibers 260, the treated fibers 270, and the plating yarn 280 described above. The plating yarns are oriented vertically and are coated with copper, zinc and/or other metals to provide an anode for an electrochemical cell. The treated fibers 470 are horizontally-oriented and shown as dark fibers. The treated fibers 470 can include filaments coated with AgNP to provide the cathode of the electrochemical cell. The non-treated fibers 460 are also horizontally-oriented and shown as lighter in color than the treated fibers 470. Said another way, in some embodiments, the tubular body 410 has a longitudinal direction AA and a circumferential direction substantially perpendicular to the longitudinal direction. The plating yarn is oriented in the longitudinal direction and the non-treated fibers 460 and the treated fibers 470 are oriented in the circumferential direction.

As shown in FIG. 5, sections of treated fibers 470 alternate with sections of non-treated fibers 460. The non-treated fibers 460 can combine with saline of an open wound to provide the salt bridge of the electrochemical cell. The number of courses of the treated fibers 470 and the non-treated fibers 460 can be modulated to adjust the electrical current produced by the compression treatment stocking system 400.

Figure 6:
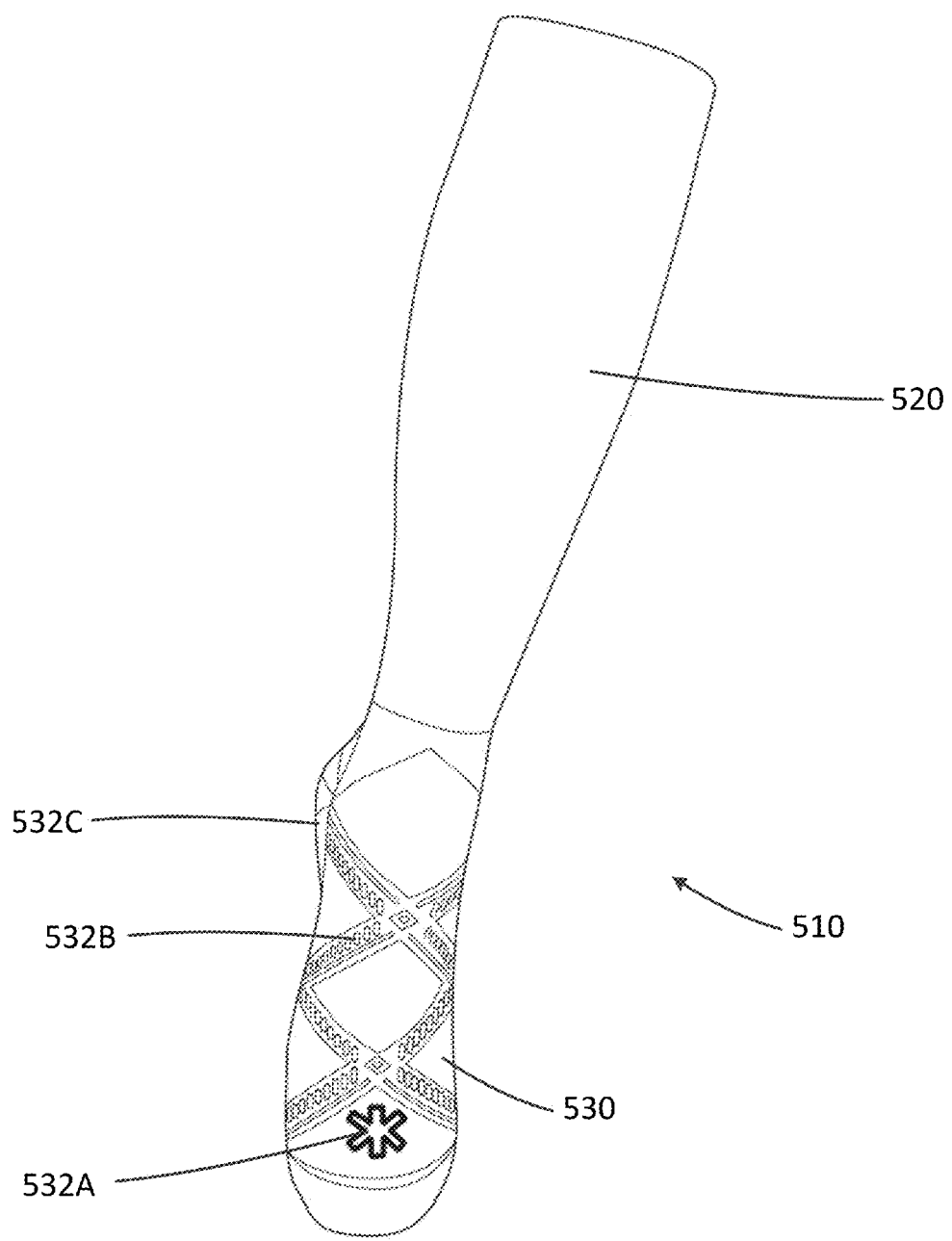
FIG. 6 is an illustration of a perspective view of a tubular body according to an embodiment.
Figure 7:
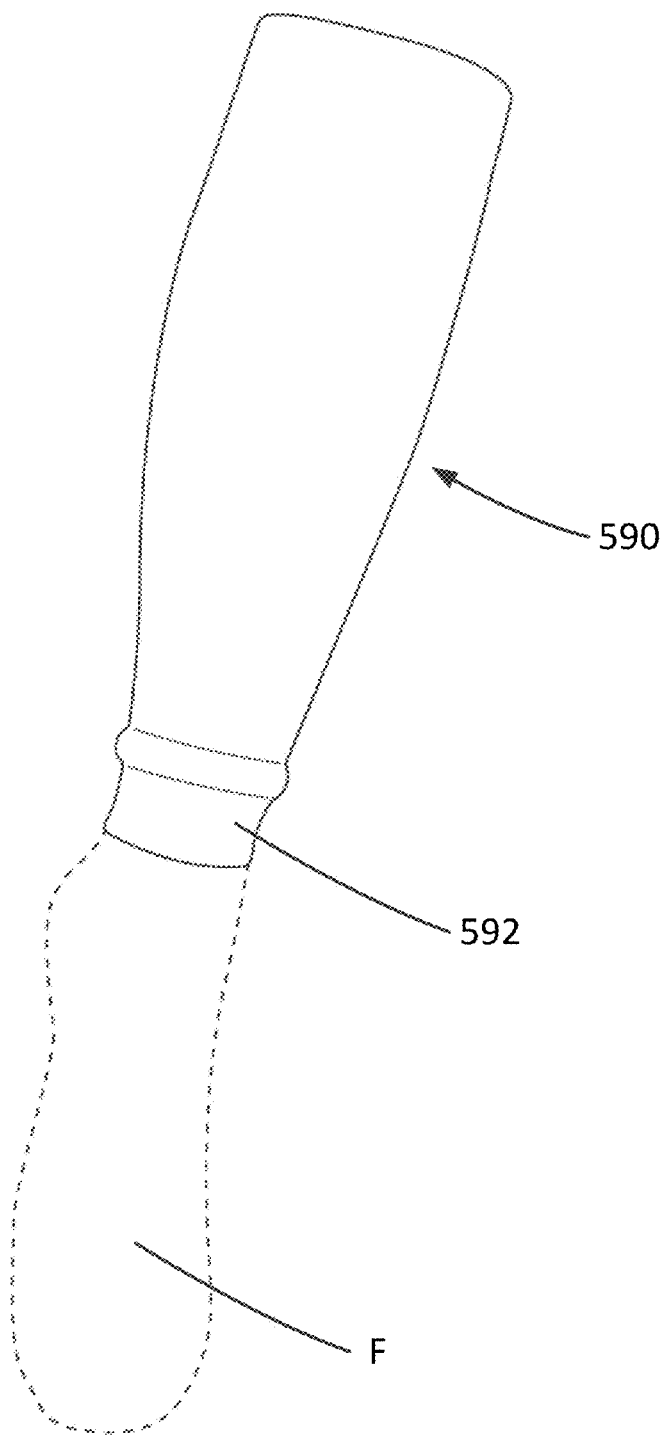
FIG. 7 is an illustration of a perspective view of a compression sleeve according to an embodiment.
Figure 8:
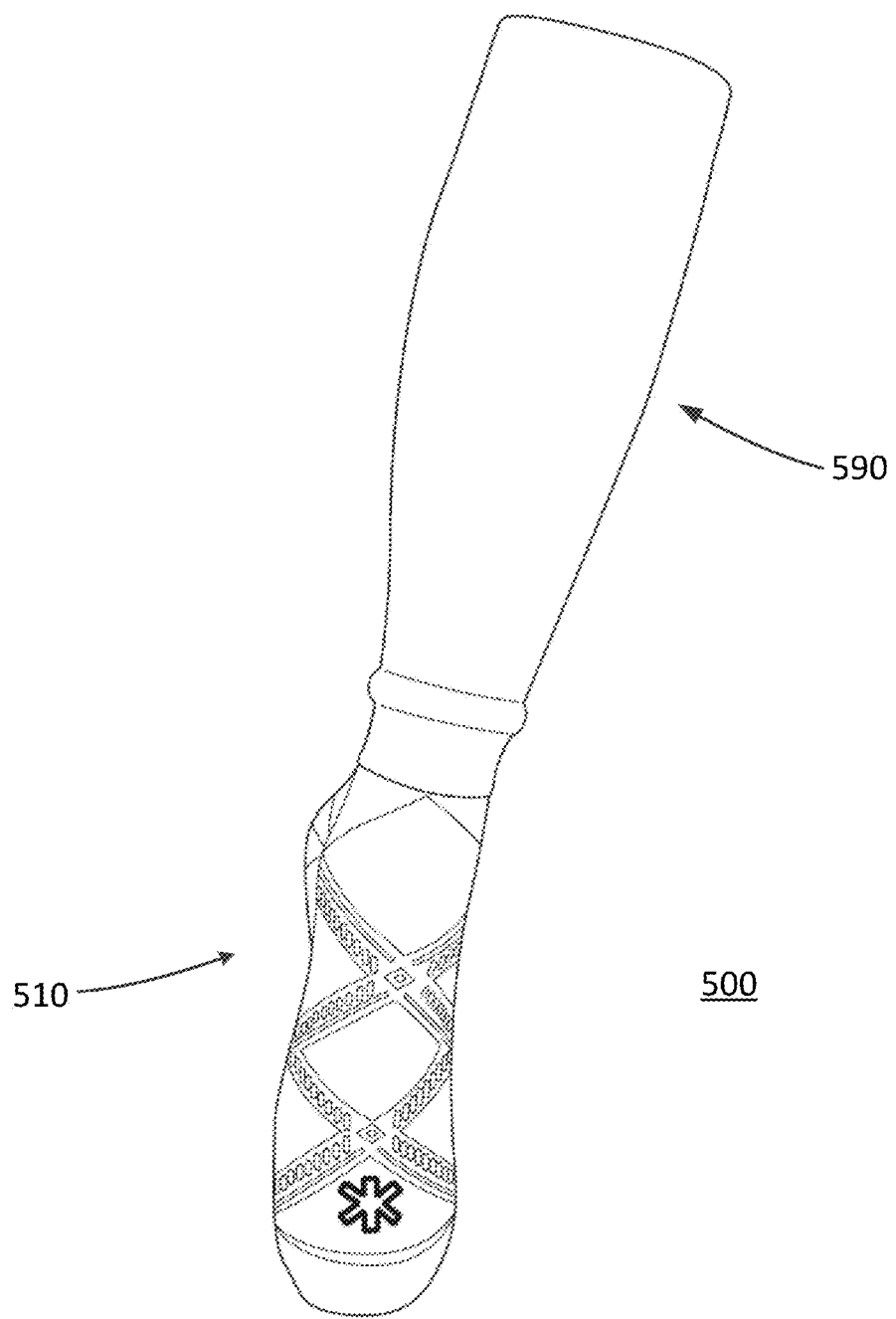
FIG. 8 is an illustration of a perspective view of a compression treatment stocking system including the tubular body of FIG. 6 and the compression sleeve of FIG. 7.

FIGS. 6-8 are illustrations of a specific embodiment of a compression treatment stocking system shown from a perspective view. A compression treatment stocking system 500 can include a tubular body 510 (i.e., a first tubular body) and a compression sleeve 590 (i.e., a second tubular body).

As shown in FIG. 6, the tubular body 510 includes a leg portion 520 and a foot portion 530. The tubular body 510 can have the same or similar characteristics to any of the tubular bodies described herein, such as tubular body 210. In particular, the leg portion 520 can have the same or similar compression characteristics to any of the leg portions described herein, such as leg portion 220. The foot portion 530 can include reinforced portions, indicated, for example, by the patterned portions 532A, 532B, and 532C.

Additionally, the tubular body 510 can have the same or similar construction characteristics as any of the tubular bodies described herein. Specifically, for example, the leg portion 520 can include an elastic welt (not shown) located at the top of the leg portion 520 (i.e., near the top of the calf of the user when worn). The elastic welt of the leg portion 520 can be formed of a 1×1 construction using a yarn with dimensions of 65 NM spun of wool and alpaca blended fiber to increase the cross stretch at the top of the leg portion 520 (i.e., near the top of the calf of the user). The remainder of the leg portion 520 can be formed of an alternating 1×1 construction with elastic. The elastic can be configured such that the leg portion 520 has a graduated compression profile from the ankle to the top of the calf of, for example, about 20 mm Hg to about 15 mm Hg. The tubular body 510 can include plating yarn running the length of the tubular body. The plating yarn (not shown) can include elastic air-coated with nylon coated with copper. Treated and non-treated wool and alpaca blended fibers (not shown) can be woven perpendicular to the plating yarn such that the treated and non-treated wool and alpaca blended fibers are arranged in a circumferential direction around the calf of the user. The treated wool and alpaca blended fibers can be coated with AgNP. The non-treated wool and alpaca blended fibers can be substantially devoid of AgNP. The non-treated wool and alpaca blended fibers can be arranged in bands that alternate with bands of the treated wool and alpaca blended fibers. For example, five courses of non-treated wool and/or alpaca can be alternated with five courses of wool and/or alpaca fibers coated with AgNP through at least a portion of the length of the leg portion 520. The wool and alpaca blended fibers can be spun into a yarn with dimensions of 1/44 NM.

The foot portion 530 can include an elastic relief pattern (not shown) in the area of the user's dorsum to decrease the pressure applied by the tubular body 510 on the nerves, tendons, and vascular structures. The foot portion 530 can also include a sandwich reinforcement in the high pressure heel and toe areas of the foot portion 530 to prevent wear. Additionally, the heel area of the foot portion 530 can be formed (e.g., knitted) in a reciprocating pattern to create a pocket for the heel of the user. The foot portion 530 can include a terry pattern on a plantar surface to provide a cushion to the plantar surface of the user's foot. The plantar surface can include a beehive hexagon patterned reinforcement portion to prevent collapse of the terry cushion. The toe area of the foot portion 530 can be closed seamlessly to prevent undesired pressure on the foot of the user.

FIG. 7 is an illustration of the compression sleeve 590 with a foot F of the user shown in phantom. The compression sleeve 590 can include the same or similar compression and construction features as described above with reference to the leg portion 520. Additionally, the compression sleeve 590 can include a welt portion 592. The welt portion 592 can be looser than the remainder of the compression sleeve 590. The compression sleeve 590 can be configured to apply a gradient compression profile from the ankle to the top of the calf of, for example, about 20 mm Hg to about 15 mm Hg.

FIG. 8 is an illustration of the compression treatment stocking system 500 in a configuration where the compression sleeve 590 is arranged over the tubular body 510. In this configuration, the combined compression profile of the leg portion 520 of the tubular body 510 and the compression sleeve 590 from the ankle to the top of the calf can be, for example, about 30 mm Hg to about 40 mm Hg. The compression sleeve 590 is configured to be applied to and removed from the tubular body 510 similarly or the same as described above with respect to the compression treatment stocking system 200.

In some embodiments, the tubular body does not include a foot portion. For example, although tubular body 210 is shown as including both the leg portion 220 and the foot portion 230, the tubular body 210 can include only a leg portion 220 such that the tubular body 210 does not cover the foot of the patient. Similarly, although tubular body 510 is shown as including both the leg portion 520 and the foot portion 530, the tubular body 510 can include only a leg portion 520 such that the tubular body 510 does not cover the foot of the patient. In other words, the tubular body can be in the form of a sock (i.e., a stocking) or a sleeve.

Additionally, any of the compression sleeves described herein can have a length that is the same as the length of the leg portion of any of the tubular bodies described herein. In other embodiments, a compression sleeve can be shorter or longer than a leg portion of a tubular body. For example, in some embodiments, the compression sleeve can extend beyond the top of the leg portion of the tubular body to at least partially cover the knee of a user. In other embodiments, the leg portion of the tubular body can extend farther up the calf of the user than the compression sleeve when arranged on a user's leg. Similarly, in some embodiments, the compression sleeve can extend farther over the ankle of the user than the leg portion of the tubular body. In other embodiments, the leg portion of the tubular body extends farther over the ankle than the compression sleeve.

In some embodiments, the tubular body and, optionally, the compression sleeve, can be configured to be applied to an arm of a user. In other embodiments, the tubular body and, optionally, the compression sleeve, can be configured to be applied to a leg of a horse or other animal.

While various embodiments of the system, methods and devices have been described above, it should be understood that they have been presented by way of example only, and not limitation. Where schematics and/or embodiments described above indicate certain components arranged in certain orientations or positions, the arrangement of components may be modified. Where methods and steps described above indicate certain events occurring in certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combination of components, other embodiments are possible having any combination or sub-combination of any features and/or components from any of the embodiments described herein. In addition, the specific configurations of the various components can also be varied. For example, the size and specific shape of the various components can be different than the embodiments shown, while still providing the functions as described herein.

What is claimed is:

1. Apparatus comprising:
a tubular body configured to be disposed around an extremity of a patient and to apply compression to the extremity, the tubular body having a longitudinal direction and a circumferential direction,
the tubular body including a treatment area having a first filament, a second filament, and a third filament, both the first filament and the second filament disposed to engage a surface of the extremity, the first filament and the third filament oriented in the circumferential direction and the second filament oriented in the longitudinal direction, the first filament arranged in a first circumferential band, the third filament arranged in a second circumferential band adjacent the first circumferential band,
the first filament including AgNP in a concentration effective to promote healing of a wound on the surface of the extremity, the second filament including a metal having a composition that forms a galvanic couple with silver, the third filament being substantially devoid of AgNP, the first filament and the second filament being arranged in the tubular body, and the AgNP and metal being arranged in the first filament and the second filament, such that the AgNP and metal form galvanic couples across at least a portion of the treatment area when in the presence of a fluid in the wound of the extremity that produce an electric current in an amount effective to further promote healing of the wound.

2. The apparatus of claim 1, wherein the metal is copper.

3. The apparatus of claim 1, wherein the metal is zinc.

4. The apparatus of claim 1, wherein the second filament is formed of a polymer, the metal being in the form of particles incorporated into the polymer.

5. The apparatus of claim 4, wherein the polymer is nylon.

6. The apparatus of claim 1, wherein the first filament is formed of wool, the AgNP being bonded to the surface thereof.

7. The apparatus of claim 6, wherein the wool is from alpaca.

8. The apparatus of claim 1, wherein the AgNP are shaped as truncated triangular plates.

9. The apparatus of claim 1, wherein the AgNP contribute less than 0.1% of the weight of the tubular body.

10. The apparatus of claim 1, wherein the tubular body has a length sufficient to extend from a foot to a knee of the extremity, and is configured to apply compression to the surface of the extremity varying from approximately 20 mm Hg at the foot to approximately 15 mm Hg at the knee.

11. The apparatus of claim 1, wherein the tubular body has an ankle pressure relief area corresponding to an ankle of the patient, to avoid iatrogenic trauma to a dorsum of the ankle.

12. The apparatus of claim 1, wherein the tubular body is a first tubular body, and further comprising a second tubular body configured to be disposed around the first tubular body and the extremity and to apply compression to the extremity.

13. The apparatus of claim 12, wherein the second tubular body is configured to extend only between an ankle and a knee of the patient.

14. The apparatus of claim 12, where in the first tubular body is configured to apply compression to the surface of the extremity varying from approximately 20 mm Hg at the foot to approximately 15 mm Hg at the knee and the second tubular body in combination with the first tubular body is configured to apply compression to the surface of the extremity varying from approximately 40 mm Hg at the foot to approximately 30 mm Hg at the knee.

15. The apparatus of claim 1, wherein the galvanic couples produce an electric voltage between 10 mV and 60 mV.

16. Apparatus comprising:
a tubular body configured to be disposed around an extremity of a patient and to apply compression to the extremity, the tubular body including a treatment area having a first filament and a second filament, both the first filament and the second filament disposed to engage the surface of the extremity, the first filament including AgNP in a concentration effective to promote healing of a wound on a surface of the extremity, the second filament including a metal having a composition that forms a galvanic couple with silver, the first filament and the second filament being arranged in the tubular body, and the AgNP and metal being arranged in the filaments, such that the AgNP and metal form galvanic couples across at least a portion of the treatment area when in the presence of a fluid in the wound of the extremity that produce an electric current in an amount effective to further promote healing of the wound, the galvanic couples producing an electric voltage between 10 mV and 60 mV.

17. The apparatus of claim 16, wherein the metal is copper.

18. The apparatus of claim 16, wherein the metal is zinc.

19. The apparatus of claim 16, wherein the second filament is formed of a polymer, the metal being in the form of particles incorporated into the polymer.

20. The apparatus of claim 19, wherein the polymer is nylon.

21. The apparatus of claim 16, wherein the first filament is formed of wool, the AgNP being bonded to the surface thereof.

22. The apparatus of claim 21, wherein the wool is from alpaca.

23. The apparatus of claim 16, wherein the AgNP are shaped as truncated triangular plates.

24. The apparatus of claim 16, wherein the AgNP contribute less than 0.1% of the weight of the tubular body.

25. The apparatus of claim 16, wherein the tubular body has a longitudinal direction and a circumferential direction, the first filament oriented in the circumferential direction and the second filament oriented in the longitudinal direction.

26. The apparatus of claim 25, wherein the first filament is arranged in a first circumferential band, wherein the treatment area further includes a third filament oriented in the circumferential direction and arranged in a second circumferential band longitudinally adjacent the first circumferential band, the third filament being substantially devoid of AgNP.

27. The apparatus of claim 16, wherein the tubular body has a length sufficient to extend from a foot to a knee of the extremity, and is configured to apply compression to the surface of the extremity varying from approximately 20 mm Hg at the foot to approximately 15 mm Hg at the knee.

28. The apparatus of claim 16, wherein the tubular body has an ankle pressure relief area corresponding to an ankle of the patient, to avoid iatrogenic trauma to a dorsum of the ankle.

29. The apparatus of claim 16, wherein the tubular body is a first tubular body, and further comprising a second tubular body configured to be disposed around the first tubular body and the extremity and to apply compression to the extremity.

30. The apparatus of claim 29, wherein the second tubular body is configured to extend only between an ankle and a knee of the patient.

31. The apparatus of claim 29, where in the first tubular body is configured to apply compression to the surface of the extremity varying from approximately 20 mm Hg at the foot to approximately 15 mm Hg at the knee and the second tubular body in combination with the first tubular body is configured to apply compression to the surface of the extremity varying from approximately 40 mm Hg at the foot to approximately 30 mm Hg at the knee.

32. The apparatus of claim 16, further comprising a third filament substantially devoid of AgNP and disposed between the first filament and the second filament, wherein the AgNP and metal form galvanic couples across the third filament.

* * * * *